(12) United States Patent
Chang et al.

(10) Patent No.: US 10,881,364 B2
(45) Date of Patent: Jan. 5, 2021

(54) PORTABLE CARBON NANOTUBE- AND FILAMENT-TYPE X-RAY APPARATUS

(71) Applicant: NANORAY CO., LTD, Daegu (KR)

(72) Inventors: Jin Young Chang, Bucheon-si (KR); Jae Yoon Park, Osan-si (KR)

(73) Assignee: NANORAY CO., LTD, Daegu (KR)

( * ) Notice: Subject to any disclaimer, the term of this patent is extended or adjusted under 35 U.S.C. 154(b) by 329 days.

(21) Appl. No.: 16/083,850

(22) PCT Filed: Mar. 17, 2017

(86) PCT No.: PCT/KR2017/002954
§ 371 (c)(1),
(2) Date: Sep. 10, 2018

(87) PCT Pub. No.: WO2017/155372
PCT Pub. Date: Sep. 14, 2017

(65) Prior Publication Data
US 2019/0059834 A1 Feb. 28, 2019

(30) Foreign Application Priority Data
Mar. 11, 2016 (KR) .................. 10-2016-0029480

(51) Int. Cl.
*A61B 6/00* (2006.01)
*A61B 6/14* (2006.01)
*H05G 1/10* (2006.01)

(52) U.S. Cl.
CPC .................. *A61B 6/14* (2013.01); *A61B 6/40* (2013.01); *A61B 6/42* (2013.01); *A61B 6/4405* (2013.01);
(Continued)

(58) Field of Classification Search
CPC .... A61B 6/14; A61B 6/40; A61B 6/42; A61B 6/4405; A61B 6/4452; H05G 1/10
See application file for complete search history.

(56) References Cited

U.S. PATENT DOCUMENTS

| | | | | |
|---|---|---|---|---|
| 6,038,287 A | * | 3/2000 | Miles | ....................... A61B 6/14 378/117 |
| 7,496,178 B2 | * | 2/2009 | Turner | ................. A61B 6/4405 378/101 |

(Continued)

FOREIGN PATENT DOCUMENTS

| KR | 10-2000-0064509 A | 11/2000 |
|---|---|---|
| KR | 10-2008-0091526 A | 10/2008 |

(Continued)

OTHER PUBLICATIONS

KR Notification of Reason for Refusal dated Jul. 11, 2011 as received in Application No. 10-2016-0029480.

(Continued)

*Primary Examiner* — Dani Fox
(74) *Attorney, Agent, or Firm* — Maschoff Brennan

(57) ABSTRACT

The present invention relates to a portable carbon nanotube- and filament-type X-ray apparatus and a method for controlling same. The present invention comprises: a control unit for controlling a portable carbon nanotube- and filament-type X-ray apparatus; and a high-voltage apparatus, of an X-ray source, which is connected to the control unit, has carbon nanotubes (CNT) applied to the high-voltage apparatus of the X-ray source, enables a low-dose exposure by means of detailed control, enables significant reduction of power consumption due to omission of filaments, and has a high-voltage capacitor and a high-voltage diode structure disposed in a sandwiched structure such that the size of the high-voltage apparatus is reduced. The present invention, which is characterized as above, provides improved image quality, assurance of long life, low power consumption, battery-less characteristic, rapid charging, a compact and lightweight structure, enhanced operability and stable exposure measures for an X-ray apparatus used mostly for dental purposes. Therefore, the present invention greatly enhances (Continued)

the reliability of the X-ray apparatus, thereby satisfying various user needs and creating a positive image.

6 Claims, 6 Drawing Sheets

(52) U.S. Cl.
CPC ... *A61B 6/4452* (2013.01); *H01J 2201/30469* (2013.01); *H05G 1/10* (2013.01)

(56) References Cited

U.S. PATENT DOCUMENTS

| | | |
|---|---|---|
| 9,788,805 B2 | 10/2017 | Oh |
| 2006/0098778 A1* | 5/2006 | Oettinger ............... H05G 1/06 378/101 |
| 2018/0184990 A1* | 7/2018 | Shin ....................... A61B 6/40 |

FOREIGN PATENT DOCUMENTS

| | | |
|---|---|---|
| KR | 10-1150157 B1 | 6/2012 |
| KR | 10-1427555 B1 | 7/2017 |
| WO | 2015-170804 A1 | 11/2015 |

OTHER PUBLICATIONS

KR Notice of Final Rejection dated Nov. 7, 2016 as received in Application No. 10-2016-0029480.

* cited by examiner

[FIG. 1]
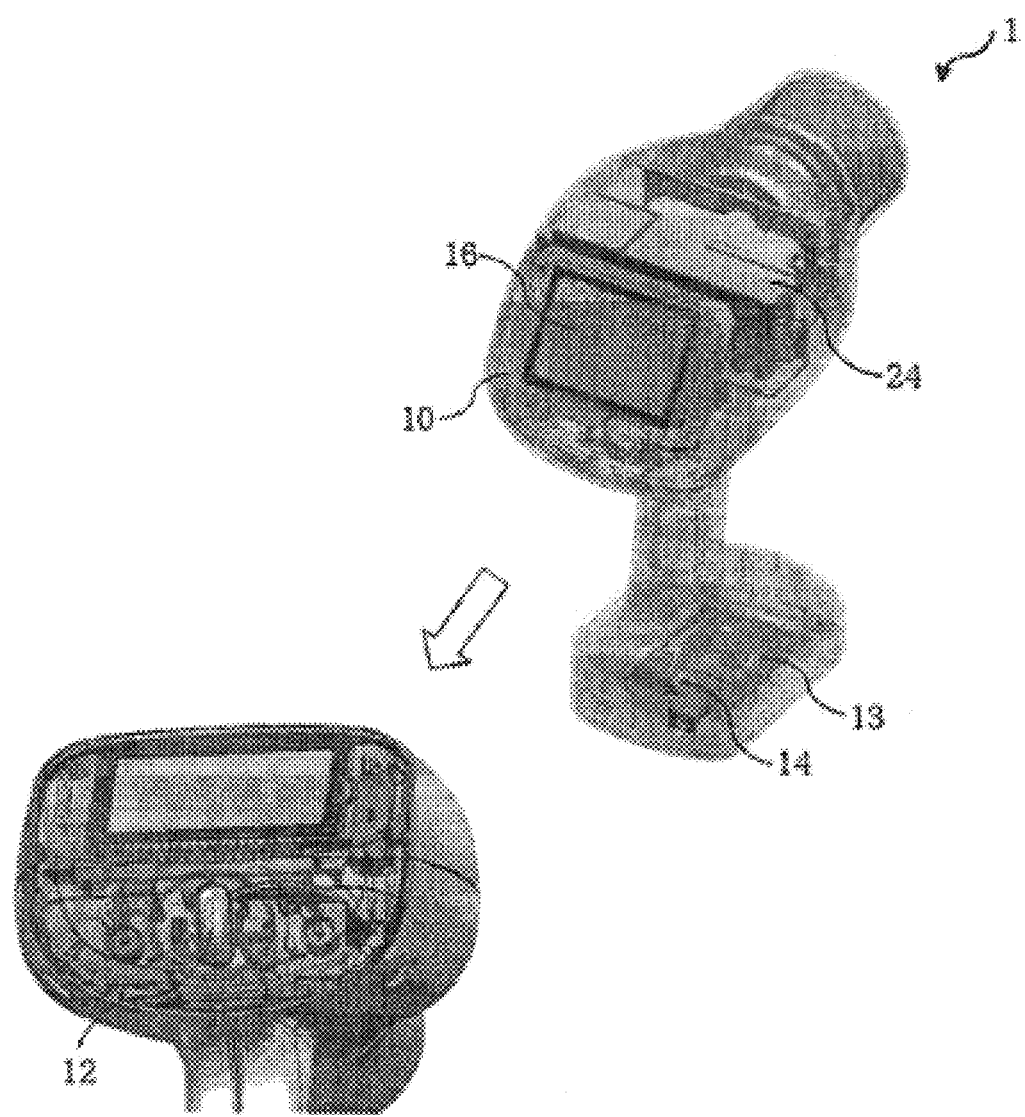

[FIG. 2]
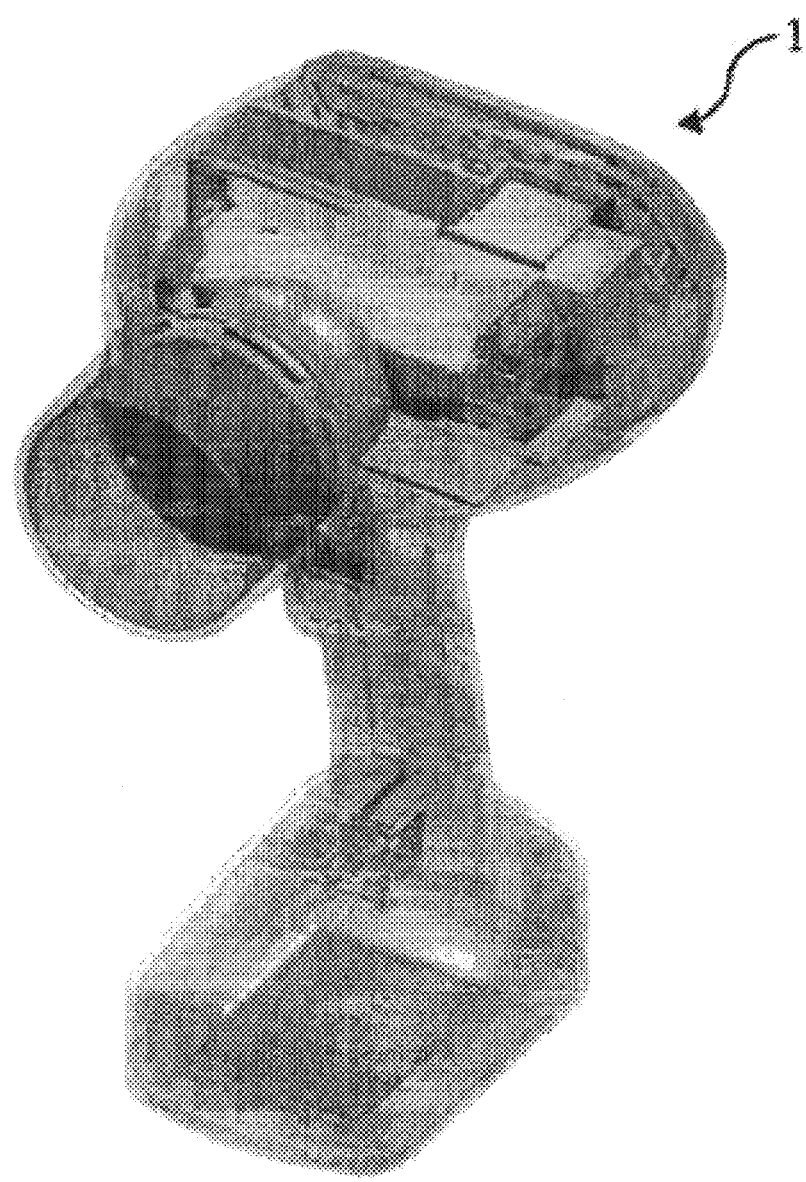

[FIG. 3]
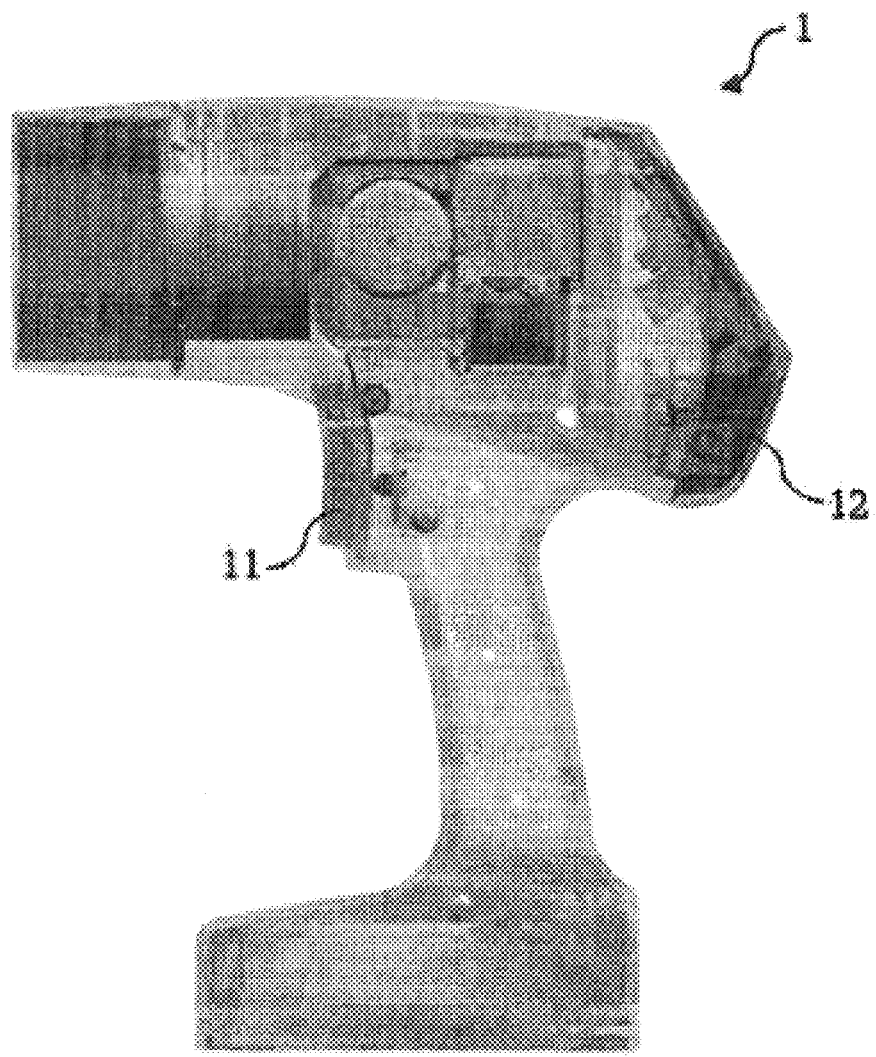

[FIG. 4]
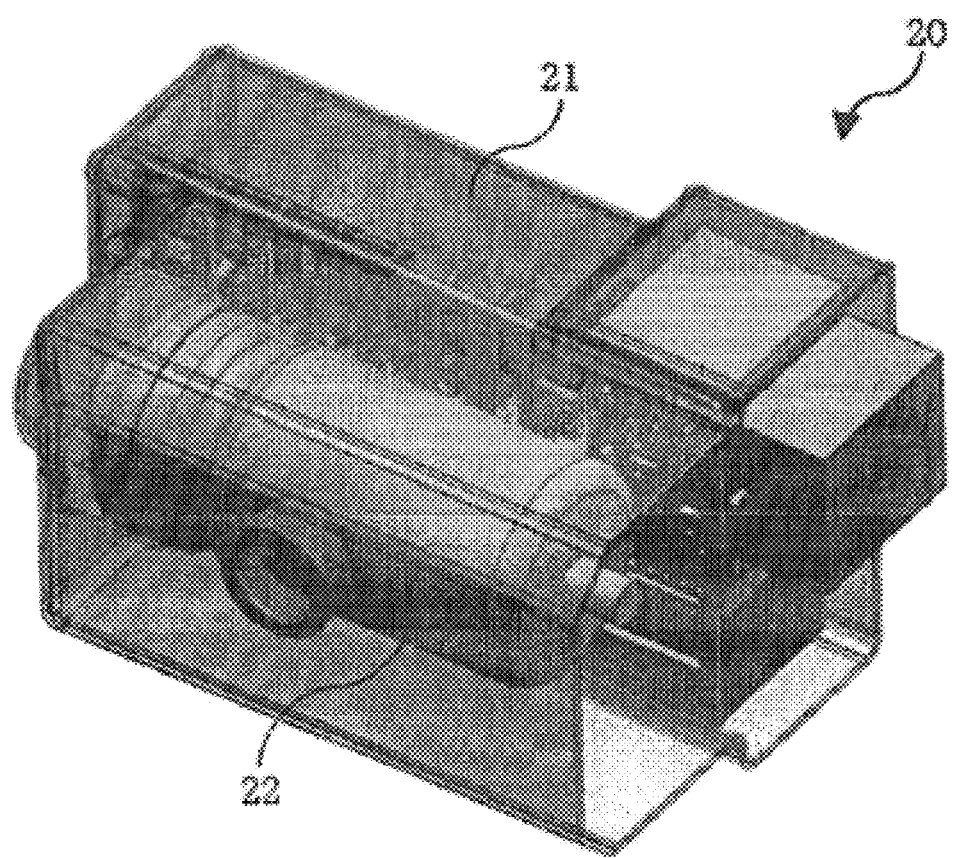

[FIG. 5]
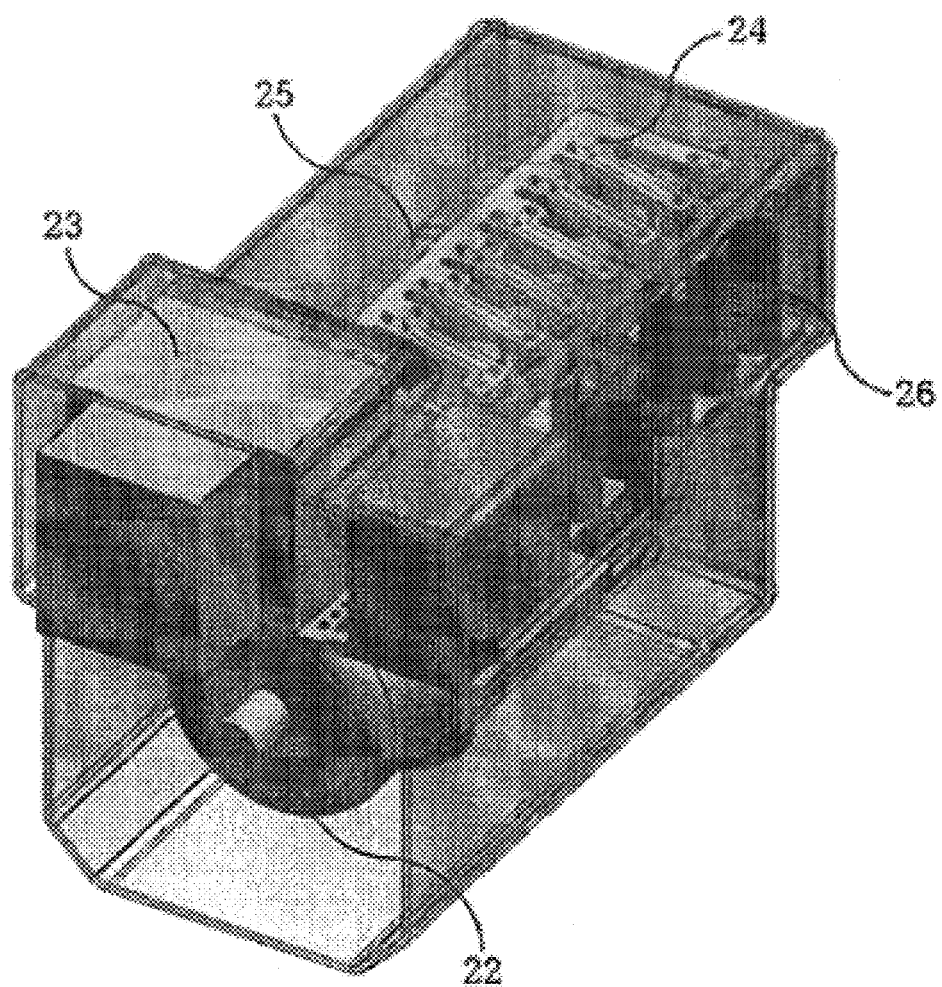

[FIG. 6]
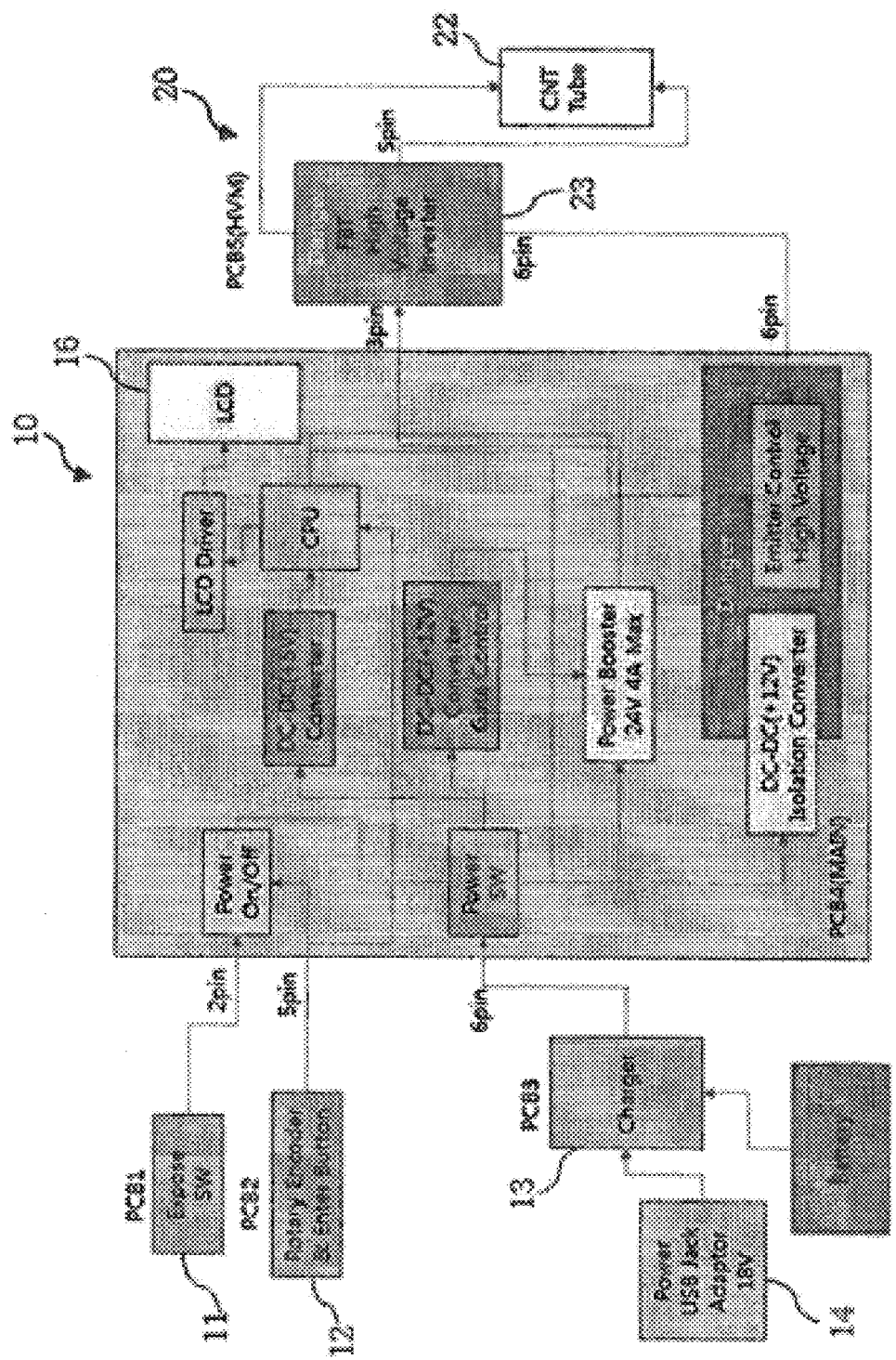

PORTABLE CARBON NANOTUBE- AND FILAMENT-TYPE X-RAY APPARATUS

TECHNICAL FIELD

The present invention relates to a portable carbon nanotube- and filament-type X-ray apparatus and more specifically, to a portable carbon nanotube- and filament-type X-ray apparatus capable of providing improved image quality, assurance of long life, low power consumption, a battery-less characteristic, a rapid charge, a compact and lightweight structure, enhanced operability and a safety measure to protect users against radiation of an X-ray apparatus used mostly for dental purposes, so as to greatly enhance the reliability of an X-ray apparatus, thereby satisfying various user needs and creating a positive image.

DESCRIPTION OF THE RELATED ART

As is well-known, a portable X-ray photographing apparatus for dental purposes was made for field warfare for the first time in 1993 in the U.S. In Japan, such a portable X-ray photographing apparatus for dental purposes is used for a patient at home such as a person with disabilities etc. in an emergency. In South Korea, since 2003, various products have been used for dental purposes considering that a patient doesn't have to move to a photographing room and can be photographed while sitting on an examining chair.

In the case of a portable X-ray photographing apparatus for dental purposes, guidelines are needed to ensure safety from radiation. This is because the hand of a person who captures an image while the person is holding such a portable X-ray photographing apparatus in the hand is likely to be exposed to radiation that leaks while a subject is photographed and because the body of the person is likely to be exposed to radiation scattered from the subject.

In recent years, such a portable X-ray photographing apparatus for dental purposes has been widely used thanks to the mobility of the apparatus within a dental examination room. The usefulness of the photographing apparatus has been recognized, in particular, in disaster areas around the world. However, such an apparatus has a problem. The problem is that a person who captures an image is exposed to radiation leaking out of a tube head and scattered from a patient because the person holds the apparatus in the hand while capturing an image.

Several studies have shown that radiation dose of a person who captures an image by using a portable X-ray photographing apparatus for dental purposes is below an annual maximum permissible dose for radiation workers. However, radiation dose of the person must be reduced by means of a radiation protection device according to the principle of keeping radiation doses to patients and personnel as low as reasonably (ALARA).

Meanwhile, the above-described conventional portable X-ray photographing apparatus for dental purposes has problems.

That is, the quality of images is poor because the focal spot of the conventional apparatus is 0.8 mm, which means images are not clearly seen.

In addition, the above-described related art consumes large amounts of electricity and experiences deterioration in performance and deformation, thereby making it hard to ensure a long life span.

Additionally, the related art preserves small amounts of energy due to high energy consumption.

Further, the related art uses a battery, and the battery of the related art needs to be replaced with a new one every six months, there by casing inconvenience to users.

Further, time to charge the related art takes four or more hours. Accordingly, it is difficult to charge the related art rapidly.

Further, the above-descried related art uses lead and insulating oil so as to shield X-rays and to ensure high-voltage insulation, thereby making it hard for the related art to have a compact and lightweight structure and making it hard to store, operate and move the related art.

Further, the related art does not provide improved operability and safety measures to protect users against radiation.

As a means to solve the above-described problems, the invention disclosed in the prior art document that will described below has been devised. However, the above-described problems have not been solved by the following invention at one stroke.

Prior Art Document (Patent Document 1) Korean Patent Registration Publication No. 1427555 (Jul. 31, 2014)

DETAILED DESCRIPTION OF THE INVENTION

Technical Problems

The present invention is devised to solve the above-described problems with the related art. The first purpose of the present invention is to provide a portable carbon nanotube- and filament-type X-ray apparatus including: a control unit for controlling a portable carbon nano x-ray tube; and a high-voltage apparatus of an X-ray source, which is connected to the control unit, to which carbon nanotubes (CNT) are applied, which enables low-dose exposure by means of duration control and detailed control, which enables a significant reduction in power consumption thanks to omission of filaments, and which has a high-voltage capacitor and a high-voltage diode disposed in a sandwich structure such that the high-voltage apparatus has a compact structure and needs a minimized mounting space. The second purpose of the present invention with the above-described technical configuration is to provide a portable carbon nanotube- and filament-type X-ray apparatus including a high-voltage apparatus of an X-ray source, to which CNTs are applied, which enables low-dose exposure by means of detailed control (technology of turning on and off an X-ray source at high speed—i.e. technology of controlling exposure time by means of duration control so as to deliver radiation only for a period of time recognized by a sensor), and which enables a significant reduction of power consumption thanks to omission of filaments. The third purpose of the present invention is to provide a portable carbon nanotube- and filament-type X-ray apparatus including a high-voltage apparatus which has a compact structure, which has a high-voltage capacitor and a high-voltage diode disposed in a sandwich structure, which is solid-molded with a silicone-based insulator with excellent thermal conductivity and insulation (about 20 kV per 1 mm) not with insulating oil so as to lighten weight and to have a compact structure, thereby making it possible to improve convenience in manipulation and management, and which is applicable not only to a CNT but also to a filament-type X-ray tube. The fourth purpose of the present invention is to provide a portable carbon nanotube- and filament-type X-ray apparatus which is configured as a battery-less apparatus, to which super capacitors are applied so as to perform the function of an immediate charge for about 1 to 10 minutes thereby reducing standby time before use, which ensures a life span of 50,000 or more hours and guarantees a constant level of performance such that the apparatus does not need to replace a battery with a new one until the life span of the apparatus expires thereby helping protecting the environment, and which is easily repaired and maintained thereby helping reduce costs and improve convenience in use. The fifth purpose of the present invention is to provide a portable carbon nanotube- and filament-type X-ray apparatus which has capacitors, a system for an immediate charge, arranged in series when usually used and performing an immediate charge by connecting with a low-voltage high-current charging circuit of each of the insulated chargers during a charge such that a charge is performed for a short period of time and that time for a charge takes less than 10 minutes thereby maximizing convenience in use. The sixth purpose of the present invention is to provide a portable carbon nanotube- and filament-type X-ray apparatus which is simply manipulated, which is configured to have a gun shape, which weighs 1.2 or less kg, which is held by one hand while a patient or an apparatus is managed readily by the other hand thereby maximizing usefulness, where exposure time, a photographing mode etc. can be controlled with one touch by one hand at the time of capturing an image thereby making it possible to conveniently manipulate the apparatus, where exposure to radiation can be manipulated by one hand by pulling the trigger of the gun-type apparatus, and which has a universal serial bus (USB) jack separately at the rear surface of the apparatus so as to synchronize and to easily connect an external device and manipulation. The seventh purpose of the present invention is to provide a portable carbon nanotube- and filament-type X-ray apparatus which can ensure safety by mixing boron oxide (B, Buraq) or boron nanotubes into an insulator as a means to restrict discharge of X-rays and to prevent a manipulator's exposure to radiation at the time of generating X-rays, where the inside of a cone for a focal spot is shielded in the shape of a lead pipe so as to discharge X-rays towards a photographed part thereby minimizing the manipulator's exposure to radiation, and where glass ($SiO_2$) and glass mixed with boron are disposed at the front of the end of the cone in the shape of a discus so as to minimize exposure to radiation. The eighth purpose of the present invention is to provide a portable carbon nanotube- and filament-type X-ray apparatus and method of controlling the same which can enhance the reliability of an X-ray apparatus, thereby satisfying various user needs and creating a positive image.

Technical Solutions

As a means to achieve the above-described purposes, a portable carbon nanotube- and filament-type x-ray apparatus of the present invention includes a control unit for controlling a portable carbon nanotube- and filament-type x-ray apparatus; and a high-voltage apparatus of an X-ray source, which is connected to the control unit, to which CNTs are applied, which enables low-dose exposure by means of detailed control, which enables a significant reduction in power consumption thanks to omission of filaments of a carbon nanotube-type x-ray apparatus, and which has a high-voltage capacitor and a high-voltage diode disposed in a sandwich structure such that the high-voltage apparatus has a compact structure and needs a minimized mounting space, wherein the control part includes a power supply source which is connected with a power switch, which stores a certain amount of electricity, to which a battery of 7 to 48 V and a super capacitor are applied, and which performs the function of an immediate charge for about 1 to 10 minutes so as to reduce standby time before use. In particular, a super capacitor ensures a prolonged life span of 50,000 or more hours and guarantees a constant level of performance such that the apparatus does not need to replace a battery with a new one until the life span of the apparatus expires thereby helping protecting the environment, and which is easily repaired an maintained thereby reducing costs and improving convenience in use. Further, a system for an immediate charge performs an immediate charge by connecting a super capacitor of 35 to 3,000 farad with a low-voltage high-current charging circuit such that a charge is performed for a short period of time and that time for a charge takes less than 10 minutes thereby maximizing convenience in use.

Advantageous Effects

As described above, a portable carbon nanotube- and filament-type x-ray apparatus of the present invention includes a control unit for controlling a portable carbon nanotube- and filament-type x-ray apparatus; and a high-voltage apparatus of an X-ray source, which is connected to the control unit, to which CNTs are applied, which enables a low-dose exposure by means of detailed control—that is, a high-voltage/high-speed switching device is arranged at the cathode so as to turn on and off X-rays at high speed—and duration control—that is, radiation is delivered only for a period of time recognized by a sensor, where an image can be captured without standby time as soon as power is turned on, and which has a high-voltage capacitor and a high-voltage diode disposed in a sandwich structure such that the high-voltage apparatus has a compact structure and needs a minimized mounting space.

The present invention with the above-described configuration includes a high-voltage apparatus of an X-ray source, to which CNTs are applied, which enables low-dose exposure by means of detailed control, and which enables a significant reduction in power consumption thanks to omission of filaments.

Further, a portable carbon nanotube- and filament-type x-ray apparatus of the present invention includes a high-voltage apparatus which has a compact structure, which has a high-voltage capacitor and a high-voltage diode disposed in a sandwich structure, which is solid-molded with a silicone-based insulator and a mixture with excellent thermal conductivity and insulation (about 20 kV per 1 mm) not with insulating oil.

Conventionally, the outer case of an X-ray source is covered with lead so as to block the discharge of X-rays. A high-voltage apparatus of an X-ray source of the present invention is molded with a mixture where a material for restricting the discharge of X-rays is mixed with an insulator so as to obtain the advantage of insulation and to ensure safety form radiation exposure in an effective way. That is, the high-voltage apparatus of an X-ray source of the present invention is solid-molded with the mixture, which is mixed with a specific polymeric material consisting of 100 parts by weight of a first resin including one or more selected from a group consisting of a polyurethane resin, a polysiloxane resin, a silicone resin, a fluororesin, an acrylic resin, and an alkyd resin; 5 to 30 parts by weight of a second resin including one or more selected from a group consisting of polyvinyl alcohol (PVA), medium-density polyethylene (MDPE), high-density polyethylene (HDPE) and low-density polyethylene (LDPE); and 5 to 30 parts by weight of polyether ether ketone (PEEK) resin powder, so as to lighten weight and to have a compact structure, thereby improving convenience in manipulation and management, and is applicable not only to a CNT but also to a filament type X-ray tube.

A high-voltage apparatus of an X-ray source of the present invention is configured as a battery-less apparatus to which a super capacitor guaranteeing a life span of 50,000 or more hours is applied thereby causing users no inconvenience caused by a charge and helping protecting the environment, and is easily repaired and maintained thereby reducing costs and improving convenience in use.

In addition, a high-voltage apparatus of an X-ray source of the present invention has super capacitors, a system for an immediate charge, which are arranged in series when usually used and performs an immediate charge by connecting with each of the insulated charging voltage devices by means of low-voltage high-current during a charge such that a charge is performed for a short period of time and that time for a charge takes less than 10 minutes thereby maximizing convenience in use.

Additionally, a high-voltage apparatus of an X-ray source of the present invention is simply manipulated, is configured to have a gun shape, weighs 1.2 or less kg, is held by one hand while a patient or an apparatus is managed readily by the other hand thereby maximize usefulness. According to the present invention, exposure time, a photographing mode etc. can be controlled with one touch by one hand at the time of capturing an image thereby making it possible to conveniently manipulate the apparatus, and exposure to radiation can be manipulated by one hand by pulling the trigger of the gun-type apparatus. Further, the present invention has a separate connector at the rear surface of the apparatus so as to synchronize and to easily connect an external device and manipulation.

Further, a high-voltage apparatus of an X-ray source of the present invention can ensure safety by shielding the inside of a cone for a focal spot in the shape of a lead pipe, in addition to a mixture where a material is mixed with an insulator, as a means to prevent a manipulator's exposure to radiation at the time of generating X-rays. According to the present invention, the inside of a cone for a focal spot is shielded in the shape of a lead pipe so as to discharge X-rays towards a photographed part thereby minimizing the manipulator's exposure to radiation, and glass ($SiO_2$) and glass mixed with boron are disposed at the end of the cone in the shape of a discus so as to minimize exposure to radiation.

The present invention having the above-described advantages can enhance the reliability of an X-ray apparatus, thereby satisfying various user needs and creating a positive image.

Preferred embodiments of the present invention as a means to achieve such purposes will be described in detail with reference to the attached drawings.

BRIEF DESCRIPTION OF THE DRAWINGS

FIG. 1 is a front perspective view of a portable carbon nanotube- and filament-type X-ray apparatus applied to the present invention.

FIG. 2 is a rear perspective view of a portable carbon nanotube- and filament-type X-ray apparatus applied to the present invention.

FIG. 3 is a front sectional view of a portable carbon nanotube- and filament-type X-ray apparatus applied to the present invention.

FIG. 4 is a front perspective view of a high-voltage apparatus of an X-ray source applied to the present invention.

FIG. 5 is a rear perspective view of a high-voltage apparatus of an X-ray source applied to the present invention.

FIG. 6 is a block diagram of a portable carbon nanotube- and filament-type X-ray apparatus applied to the present invention.

DESCRIPTION OF THE SYMBOLS

1: Portable carbon nanotube- and filament-type X-ray apparatus
10: Control unit
20: High-voltage apparatus of an X-ray source

BEST MODE FOR CARRYING OUT THE INVENTION

A portable carbon nanotube- and filament-type X-ray apparatus applied to the present invention is configured as in FIGS. 1 to 6.

In describing the present invention, detailed description of known functions and configurations will be omitted if they are deemed to make the gist of the present invention unnecessarily vague.

Additionally, terms that will be described hereafter are the ones determined considering functions in the present invention. The terms can be changed in accordance with the intention and practice of a manufacture. The terms should be defined on the basis of the contents throughout the specification.

Further, the size and thickness of each element illustrated in the drawings may be exaggerated for the sake of convenience in description. Accordingly, the present invention is not necessarily limited to what is illustrated in the drawings.

First, a portable carbon nanotube- and filament-type X-ray apparatus of the present invention, as illustrated in FIGS. 1, 2 and 3, includes a control unit 10 for controlling a portable carbon nanotube- and filament-type X-ray apparatus 1.

Additionally, a portable carbon nanotube- and filament-type X-ray apparatus of the present invention includes a high-voltage apparatus of an X-ray source 20, which is connected to the control unit 10, to which CNTs are applied, which enables low-dose exposure by means of detailed control, which enables a significant reduction in power consumption thanks to omission of filaments of a carbon nanotube-type X-ray apparatus, and which has a high-voltage capacitor 25 and a high-voltage diode 26 disposed in a sandwich structure, as illustrated in FIG. 5, such that the high-voltage apparatus has a compact structure and needs a minimized mounting space. However, the high-voltage capacitor 25 and high-voltage diode 26 are omitted in FIG. 6 because the high-voltage capacitor 25 and high-voltage diode 26 are illustrated in FIG. 5 and because FIG. 6 is a block diagram.

The control part includes a power supply source which is connected with a power switch, which stores a certain amount of electricity, to which a battery and a super capacitor of 7 to 48 V are applied, and which performs the function of an immediate charge for about 1 to 10 minutes so as to reduce standby time before use. In particular, a super capacitor ensures a life span of 50,000 or more hours and guarantees a constant level of performance such that the apparatus does not need to replace a battery with a new one until the life span of the apparatus expires thereby helping protecting the environment, and is easily repaired an maintained thereby reducing costs and improving convenience in use. Further, a system for an immediate charge performs an immediate charge by connecting a super capacitor of 35 to 3,000 farad with a low-voltage high-current charging circuit such that a charge is performed for a short period of time and that time for a charge takes less than 10 minutes thereby maximizing convenience in use.

In particular, the high-voltage apparatus (flyback transformer (FBT)), (High Voltage Inverter (HVM)) of an X-ray source 20 applied to the present invention is configured as follows.

That is, a portable carbon nanotube- and filament-type X-ray apparatus of the present invention includes a high-voltage transformer (FBT) 23 inside a body 21.

Further, a portable carbon nanotube- and filament-type X-ray apparatus of the present invention includes a high-voltage module 24 provided with a plurality of high-voltage capacitors 25 and high-voltage diodes 26 which are provided inside the body 21 so as to generate high-voltage direct currents (DC) supplied to an X-ray CNT tube.

In addition, a portable carbon nanotube- and filament-type X-ray apparatus of the present invention includes X-ray CNTs 22 which are provide in the body 21, which are configured to have a vacuum pipe shape having an anode and a cathode or an emitter, to which a high-voltage power at a constant level is supplied and in which the anode radiates an X-ray when a filament or emitter discharges electrons.

Additionally, according to the high-voltage apparatus of an X-ray source 20 applied to the present invention, a material such as a polymeric material for restricting the discharge of X-rays is mixed for molding so as to obtain the advantage of insulation and to ensure safety from radiation exposure in an effective way, wherein the high-voltage module is integrated and solid-molded by means of a first resin including one or more selected from a group consisting of a polyurethane resin, a polysiloxane resin, a silicone resin, a fluororesin, an acrylic resin, and an alkyd resin; a second resin including one or more selected from a group consisting of polyvinyl alcohol (PVA), medium-density polyethylene (MDPE), high-density polyethylene (HDPE) and low-density polyethylene (LDPE); and powder in which a polyether ether ketone (PEEK) resin is contained in the first and second resins.

Further, the control unit 10 applied to the present invention is technically configured as follows.

That is, a portable carbon nanotube- and filament-type X-ray apparatus of the present invention, as illustrated FIGS. 4, 5 and 6, includes a liquid crystal display (LCD) 16 which is connected with an LCD driver for a display.

Further, a portable carbon nanotube- and filament-type X-ray apparatus of the present invention includes an exposure switch 11 which is connected with a power on/off switch such that X-rays are discharged when a trigger is pulled.

Further, a portable carbon nanotube- and filament-type X-ray apparatus of the present invention includes a rotary encoder and an enter button 12 which are connected with the power on/off switch and a central processing unit (CPU) so as to execute the setting of conditions for capturing an image and to control power.

In this case, the rotary encoder and enter button are preferably configured to change an amount of time for capturing an image, call and save a user memory address, and change a mode for an adult and a child by using a wheel-type rotary encoder.

Finally, the control unit 10 applied to the present invention includes a charger 13 which is connected with a power switch and stores a certain amount of electricity so as to stabilize power supply.

In this case, the charger 13 is configured as a charging board which immediately supplies high current to a battery and super capacitor for a charge, is optimum for a lithium-ion battery, performs a charge at 2.5 A at every hour, uses five capacitors of 2.7 V in a serial connection when charging a super capacitor, and immediately charges each cell at 5 to 10 A by using the output of each insulated transformer for a charge.

Additionally, a portable carbon nanotube- and filament-type X-ray apparatus of the present invention includes a power adaptor jack 14 which is connected with the charger 13 and is used to capture an image by connecting with an adapter or to supply power to a charging device.

In terms of a DC-DC (+5V) converter in the drawings, power of 5V, 18 to 24V is always supplied to the DC-DC (+5V) converter although a wide range of power such as power of 8 to 32V is applied from the outside. A CPU is an 8-bit micro controller unit (MCU), and an LCD driver is a HT1621 LCD driver so as to display various kinds of information. Further, the LCD is an LCD for displaying a portable X-ray control, and displayed information includes an amount of time spent on exposure, an adult and a child exposed to radiation, an exposure state during exposure, a memory mode, a battery level and information on an alarm etc. A power booster has input voltages of a maximum of 8 to 18V and an output voltage of a maximum of 24 V at 5 A. Further, a DC-DC (+12V) isolation converter has input voltages of a maximum of 8 to 18V and an output voltage of a maximum of 12 V at 1 A, and an emitter is turned on and off by means of a high voltage of 2 KV (filaments do not). Power is supplied to the DC-DC (+12V) isolation converter for an immediate charge by connecting six batteries of 3.7 V or six to nine super capacitors of 2.7 V.

Meanwhile, a portable carbon nanotube- and filament-type X-ray apparatus of the present invention can be variously modified and formed in applying the above-described configuration.

Additionally, it should be understood that the present invention is not limited to specific embodiments that have been described in the detailed description of the invention. Rather, it should be understood that the present invention includes all the modifications, equivalents and alternatives within the spirit and scope of the present invention defined in the appended claims.

Advantages of a portable carbon nanotube- and filament-type X-ray apparatus of the present invention with the above-described configuration will be described as follows.

Above all, the present invention has the advantage of providing improved image quality, assurance of long life, low power consumption, a battery-less characteristic, a rapid charge, a compact and lightweight structure, enhanced operability of an X-ray apparatus used mostly for dental purposes and a safety measure to protect users against radiation of an X-ray apparatus.

FIG. 1 is a front perspective view of a portable carbon nanotube- and filament-type X-ray apparatus applied to the present invention, FIG. 2 is a rear perspective view of a portable carbon nanotube- and filament-type X-ray apparatus applied to the present invention, and FIG. 3 is a front sectional view of a portable carbon nanotube- and filament-type X-ray apparatus applied to the present invention.

In additional, FIG. 4 is a front perspective view of a high-voltage apparatus of an X-ray source applied to the present invention, and FIG. 5 is a rear perspective view of a high-voltage apparatus of an X-ray source applied to the present invention.

Further, FIG. 6 is a block diagram of a portable carbon nanotube- and filament-type X-ray apparatus applied to the present invention.

In particular, a main printed circuit board (PCB) applied to the present invention is configured as a 4 layer epoxy PCB, and a rotary encoder applied to the present invention is configured as a wheel-type rotary encoder so as to change an amount of time for capturing an image, call and save a user memory address, change a mode for an adult, a child etc.

Additionally, in terms of an exposure switch 11, a switch is disposed at a position corresponding to that of the trigger of a gun, and the trigger is pulled by the index finger so as to discharge X-rays.

In addition, a USB jack disposed at the rear of the apparatus is configured to be linked with another device so as to capture an image by using X-rays without pressing the exposure switch.

Further, a power adaptor jack 14 connects with a DC 12V adaptor so as to capture an image or to supply power to a charging device.

Further, an enter button performs two functions. The enter button turns power on and off, and calls and save memory. When the enter button is pressed for 0.5 or more seconds in the state where power is turned off, power is immediately turned on, and when the enter button is pressed for 4 or more seconds, power is turned off.

Further, in terms of calling and saving memory information, when the enter button is briefly pressed in the state where power is turned on, stored information is called in four stages. The rotary encoder is rotated so as to change an amount of time etc., and then the enter button is pressed for about two seconds so as to store information.

That is, when a user stores conditions for capturing an image in four pieces of memory or calls pre-stored conditions for capturing an images from memory, when a mode etc. is changed for an adult, a child etc. the enter button is used.

Additionally, when power is turned off, a small amount of uA current flows. Accordingly, even if power is turned off for about six months, complete discharge does not occur.

Finally, if the apparatus does not perform any operation, power is automatically turned off after 30 seconds.

Meanwhile, to operate an apparatus of the present invention, a user holds a portable carbon nanotube- and filament-type X-ray apparatus 1 and turns on the rotary encoder and enter button 12.

Then, the LCD 16 of the portable carbon nanotube- and filament-type X-ray apparatus 1 is initialized, and memory is loaded by the control unit 10.

Then, the buttons of rotary rotation up→rotary rotation down→exposure switch 11 operation→the enter button 12 of the X-ray apparatus are not pressed, operations are consecutively performed as described. When the button of rotary rotation up is pressed, set time goes up, and when the button of rotary rotation down is pressed, set time goes down.

Further, when the button of exposure switch 11 operation is pressed, operations are consecutively performed from filament on→delay 1 sec→H-volt on→delay set time→H-Volt off.

Additionally, when the enter button 12 is pressed, operations are consecutively performed from memory address-→memory load.

The above-described present invention has a high-voltage apparatus of an X-ray source to which CNTs are applied, which enables low-dose exposure by means of detailed control, which enables a significant reduction in power consumption thanks to omission of filaments, and which has a high-voltage capacitor and a high-voltage diode disposed in a sandwich structure such that the high-voltage apparatus has a compact structure.

INDUSTRIAL APPLICABILITY

The realization of the present invention can facilitate technical advancements and make contribution to industrial advances. Accordingly, the technical spirit of a portable carbon nanotube- and filament-type X-ray apparatus of the present invention deserves protection.

The invention claimed is:

1. A portable carbon nanotube- and filament-type x-ray apparatus comprising:
   a control unit for controlling a portable carbon nanotube- and filament-type x-ray apparatus; and
   a high-voltage apparatus of an X-ray source, which is connected to the control unit, to which carbon nanotubes (CNT) are applied, which enables low-dose exposure by means of detailed control, which enables a significant reduction in power consumption thanks to omission of filaments of a carbon nanotube-type x-ray apparatus, and which has a high-voltage capacitor and a high-voltage diode disposed in a sandwich structure such that the high-voltage apparatus has a compact structure and needs a minimized mounting space,
   wherein the control part comprises a power supply source which is connected with a power switch, which stores a certain amount of electricity, to which a battery and a super capacitor of 7 to 48 V are applied, and which performs the function of an immediate charge for about 1 to 10 minutes so as to reduce standby time before use, the super capacitor ensures a life span of 50,000 or more hours, guarantees a constant level of performance such that the apparatus does not need to replace a battery with a new one until the life span of the apparatus expires thereby helping protecting the environment, and is easily repaired and maintained thereby reducing costs and improving convenience in use, and a system for an immediate charge performs an immediate charge by connecting a super capacitor of 35 to 3,000 farad with a low-voltage high-current charging circuit such that a charge is performed for a short period of time and that time for a charge takes less than 10 minutes thereby maximizing convenience in use.

2. The portable carbon nanotube- and filament-type X-ray apparatus according to claim 1, the high-voltage apparatus of an X-ray source comprising:
   a high-voltage transformer (FBT; fly back transformer) provided inside a body;
   a high-voltage module comprising: a plurality of high-voltage capacitors and high-voltage diodes which are provided inside the body so as to generate high-voltage direct currents (DC) supplied to X-ray CNTs; and X-ray CNTs which are provide in the body, which is configured to have a vacuum pipe shape having an anode and a cathode or an emitter, to which a high-voltage power at a constant level is supplied, and in which the anode radiates X-rays when a filament or an emitter discharges electrons.

3. The portable carbon nanotube- and filament-type X-ray apparatus according to claim 2, wherein the high-voltage apparatus of an X-ray source is molded with a material mixed with a polymeric material for restricting the discharge of X-rays so as to obtain the advantage of insulation and to ensure safety from radiation exposure in an effective way, the polymeric material is used to integrate and solid-mold the high-voltage module by means of a first resin comprising: one or more selected from a group consisting of a polyurethane resin, a polysiloxane resin, a silicone resin, a fluororesin, an acrylic resin, and an alkyd resin;

a second resin comprising one or more selected from a group consisting of polyvinyl alcohol (PVA), medium-density polyethylene (MDPE), high-density polyethylene (HDPE) and low-density polyethylene (LDPE); and powder in which a polyether ether ketone (PEEK) resin is contained in the first and second resins.

4. The portable carbon nanotube- and filament-type X-ray apparatus according to claim 1, the control unit comprising:

a liquid crystal display (LCD) which is connected with an LCD driver for a display;

an exposure switch which is connected with a power on/off switch such that X-rays are discharged when a trigger is pulled; and a rotary encoder and an enter button which are connected with the power on and off switch and a central processing unit (CPU) so as to execute the setting of conditions for capturing an image and to control power.

5. The portable carbon nanotube- and filament-type X-ray apparatus according to claim 1, the control unit comprising:

a charger which connects with a power switch and stores a certain amount of electricity so as to stabilize power supply; and a power adaptor jack which connects with the charger and is used to capture an image by connecting with an adapter or to supply power to a charging device.

6. The portable carbon nanotube- and filament-type X-ray apparatus according to claim 4, wherein the rotary encoder and enter button are configured to change an amount of time for capturing an image, call and save a user memory address, and change a mode for an adult and a child by means of a wheel-type rotary encoder.

* * * * *